United States Patent [19]

Siegler et al.

[11] Patent Number: 5,340,737
[45] Date of Patent: Aug. 23, 1994

[54] PROCESS OF PREPARING PEPSIN FOR BATING HIDES

[76] Inventors: Marcel Siegler, 7855 Blvd. East, North Bergen, N.J. 07047; Mihai Deselnicu, 1 Blvd. Tineretului, Bucharest, Romania; Victoria Bratulescu, 16 Sibiului Street, Bucharest, Romania; Andrei Anghel, Zona Bucovina Bloc B20, Timisoara, Romania

[21] Appl. No.: 74,882

[22] Filed: Jun. 10, 1993

[51] Int. Cl.$^5$ .......................... C12N 9/64; C12N 9/48; C12N 9/50; A61K 37/54
[52] U.S. Cl. .................... 435/226; 435/212; 435/219; 435/814; 424/94.66
[58] Field of Search ............... 435/212, 219, 226, 814; 424/94.66

[56] References Cited

U.S. PATENT DOCUMENTS

| | | | |
|---|---|---|---|
| 220,745 | 10/1879 | Ball | 424/94.66 |
| 286,138 | 10/1883 | Jensen | 435/226 |
| 327,567 | 10/1885 | Manwaring | 424/94.66 |
| 338,471 | 3/1886 | Blumenthal | 435/226 |
| 414,591 | 11/1889 | Russell | 435/226 |
| 424,357 | 3/1890 | Russell | 435/226 |
| 433,395 | 7/1890 | Brill | 425/226 |
| 449,839 | 4/1891 | Webber | 435/226 |
| 454,575 | 6/1891 | Webber | 435/226 |
| 2,305,714 | 10/1939 | Keil | 435/226 |
| 2,701,228 | 2/1955 | McKerns | 435/226 |
| 3,549,501 | 12/1970 | Trautman et al. | 435/226 |
| 4,254,535 | 3/1981 | Pedersen et al. | 452/106 |
| 4,436,724 | 3/1984 | Ohnishi et al. | 424/85.8 |
| 5,151,358 | 9/1992 | Heinsohn et al. | 435/226 |

FOREIGN PATENT DOCUMENTS

| | | | |
|---|---|---|---|
| 1370137 | 12/1985 | U.S.S.R. | 435/226 |
| 700715 | 6/1951 | United Kingdom | 435/226 |

OTHER PUBLICATIONS

Jurgen Christner; "The Use of Lipases in the Beamhouse Process"; 87th ann.meeting, New Hampshire Jun. 16-20, 1991; pp. 128-140.

K. T. W. Alexander; "The 1988 John Arthur Wilson Memorial Lecture", Enzymes in the Tannery, Moulton Park, England; pp. 287-316.

T. J. Cooper; "The First One Hundred Years of Commercial Anzymes", Atkin Memorial Lecture; 25 Ansell Way, Hardingstone, Engl., 5 pages.

Pancreol Bate Fas, Hodgson (only information available).

Merck Biochemica, Pepsin from Porcine Mucosa.

Rohm, Darmstasdt, Leather Technology, Enzymatic Bating Agent for the Acid Bate, two pages (Aug. 24, 1990).

Primary Examiner—Douglas W. Robinson
Assistant Examiner—Jon P. Weber
Attorney, Agent, or Firm—Herbert Dubno; Jonathan Myers

[57] ABSTRACT

The preparation of a pepsin extract from the stomach of pigs, sheep or cattle, which is suitable for the bating of hides, is presented. The process involves macerating the stomach mucous, sedimenting the material, reserving the middle layer for pharmaceutical preparation, combining the other two layers, drying them and adding salt for preservation. The resulting pepsin containing material is particularly suitable for acid enzymic bating of chrome tan hides after the pickle process with the main purpose of obtaining a higher surface yield and a softer leather.

4 Claims, No Drawings

PROCESS OF PREPARING PEPSIN FOR BATING HIDES

FIELD OF THE INVENTION

This invention relates to a procedure of bating the hides and skins under acid conditions after the pickling process and particularly the bating of wet blue chrome tanned hides or skins with a pepsin enzyme product. The application of this enzymatic procedure under acid conditions in the tanneries, refers to the bating of pickled hides or skins and particularly to the chrome tanned hides and skins with the main purpose of increasing the surface yield and making softer, fuller leather and better color uniformity.

DESCRIPTION OF THE PRIOR ART

Enzyme utilization in the tannery for processing hides and skins has been known for many years. The bating procedure under the alkaline conditions which consists of using a proteolytic enzyme; pancreatic proteases (trypsin) is today universally recognized by the entire leather industry. This type of enzyme treatment to be effective should be conducted at a temp. of 35 to 38° (95°-105° F.) and at a pH of 7.5-8.5, otherwise the enzyme efficiency drops drastically.

The other bating enzymes which are employed in the leather industry, are fungal or bacterial in origin.

An industrial bating agent usually contains: enzymes, sawdust or china clay as a carrier, buffer salt and deliming salt such as ammonium sulfate.

It is well known that the purpose of the bating is the loosening and peptization of the skin fibrous structure through the removal of degraded collagen and the residues of the inter-fibrillary proteins and epidermis. The enzyme should provide the opening up of the hide collagen without attacking the grain layer, making the final leather softer with greater stretch.

The effect of bating enzymes occurs through the diffusion of the enzyme through the hide or skin.

The greatest concentration of enzymes is found on the outer layers. On the unsplit pelts, the penetration of the enzyme on the inside of the hide is very low and therefore not enough effect can be expected on the hide substance, because the bating enzymes do not reach the inner zones of the hide. This is particularly so in the neck and butt areas.

Insufficient bating results in the failure to remove nonfibrous proteins, causing a generation together of the fibers when the leather is dried.

The result is firmer leather with a cracky, dirty grain and lack of flexibility. The bating should also have an effect of progressive weakening of the elastin fiber network to reduce the coarse grain and the thickness of the grain which will become smoother and more relaxed; conversely, over-bating the hides produces stretchier, looser grains, spongy and empty flanks with a poor gain break. The efficiency activity of the enzyme under alkaline conditions depends not only on the type and concentration of the enzyme but also on the temperature, pH, volume and running time of the bating process. Therefore this enzyme treatment is considered a sensitive process, does not assure quality, uniformity from drum to drum (batch to batch) and even from hide to hide and results in a large variation of leather characteristics.

According to Jurgen Christner's paper: "Second generation of bating agents" presented at the IULTCS Congress in 1991 in Barcelona, in the last decade a second generation of pancreatic bating agents was developed with very specific activity in a new form, a liquid stable and suitable for automatic dosing in the tannery process.

The different classes of enzymes: pancreatic, bacterial and fungal are today developed; each one acts at different pH ad temperature. While pancreatic protease is active between pH 7.5-8.5, fungal protease between pH 3.5-5.0 bacterial protease acts starting at a pH of 6 and even is active under in alkaline conditions (pH 10-11).

DETAILED DESCRIPTION OF THE INVENTION

"Hide" as used herein means and refers to hides such as bovine, bulls, buffalo and the like as well skins such as goat, sheep, deer, pig, reptile and the like.

The enzyme product is pepsin which is extracted from red stomach mucous of pigs, cattle or sheep.

The enzyme of the present invention is obtained from the byproducts of a pharmaceutical and/or food grade pepsin extract and has application in the tannery as an acid bating product during the pickling process and more particularly, on split and shaved chrome tanned hides, with the main purpose of obtaining a higher surface yield and making softer, more uniform quality leather.

The known procedure of an acid bating product is based on the use of the purified enzymes obtained from microbial or mammalian sources: These enzymes are obtained through microbial biosynthesis or extracted from mammalian organs, purified and mixed with different preserving agents. The procedure of purification is very costly because it has the disadvantage of decreasing the yield of the active enzyme According to the present invention, the procedure of extracting the pepsin enzyme eliminates the above disadvantages because the raw material is the byproduct resulting from the preparation of a food or pharmaceutical grade pepsin and this reduces to a minimum the purification process.

The enzymatic product is obtained through maceration of the red mucous stomach of pigs, cattle or sheep under acid conditions.

A liquid extract with 16-18% dry material (DM) is obtained by a sedimentation process. Because of different degrees of density three distinct phases are obtained: The clear extract phase is used for the preparation of a food or pharmaceutical grade of pepsin, highly purified, while the other two phases are considered byproducts by the food or pharmaceutical industry.

The present invention uses these byproducts as raw material for the preparation of a dry enzymatic product with a proteolytic activity of 0.2-0.6 units FIP/mg pepsin extract. This enzymatic product has application in the tanneries as an acid bating composition after the pickling process of chrome tan (wet blue) hides or skins.

The enzyme treatment under acid conditions according to the present invention, can be also conducted at lower temperatures such as 18°-25° C., while under the classical alkaline bating condition the activity of the enzyme drops sharply at temperatures under 30° C. According to this present invention, the enzymatic treatment under acid conditions eliminates the alkaline bating disadvantages and improves the quality of the chrome tanned (wet blue) stock. The leathers are softer and a surface yield increase of 3 to 5% is obtained, according to the thickness and type of leather provided. The color of the leather is also more uniform.

The purpose of this invention is to obtain from the byproducts of the pepsin extraction for food grade or pharmaceutical industry, an acid bating product at a lower cost which can be applied in the process of making leather, after pickling or on chrome tanned leather. The most important advantages of using the acid enzymatic product are softer leather, higher surface yield and better color uniformity. Also this enzymatic procedure eliminates all the disadvantages of the alkaline bating described above.

Another significant advantages is the use of this acid enzyme on pig and sheep skins which are very greasy. The proteolytic action of this enzyme degrades the cell membranes and the grease is eliminated, which means the enzyme actually also acts as a degreasing agent. According to the type of leather and the degree of softness required, the fact that this acid enzyme gives softer leather, means that the amount of fat liquor used in the tannery can be reduced.

The preparation of the acid enzyme product, according to the present invention: To a stainless steel vessel with 300 kg of pig red stomach mucous is added 10-15 l 37% HCl under continuous agitation until a pH of 2.0-2.5 is obtained. Then the material is stirred at 60 RPM for another 12 to 18 hours until complete maceration; next a sedimentation time of 24-48 hours is allowed until a distinct separation of three phases takes place, because of different density. The middle clear liquid phase is separated and approximately 150 to 200 l of pepsin extract are obtained, with a proteolytic activity of 80-100 FIP units/ml. This extract is then used for the preparation of a food grade or pharmaceutical grade of highly purified pepsin. The other two phases of approx. 100 to 120 l of viscous liquid which contain pepsin, hydrolyzed proteins and lipids are mixed together, which have a proteolytic activity of 60 to 80 FIP units/and 15 to 18% D.M. At this time, the extract is dried by one of the known methods (as atomizer, blow jet air etc.). 15-20 kg. of dry product is obtained with a proteolytic activity of 0.2 to 0.6 FIP units/mg. This dry product is used with 10 to 20% NaCl for preservation, then ground—if necessary—weighted and packed.

The enzymatic activity of pepsin is determined by the Merck Biochemical method which is expressed as FIP units/mg. Pepsin is a characteristic enzyme of the mammalian red mucous stomach, with optimum activity at a pH around 2, with a molecular weight of 35000 and a large amount of dicarboxylic aliphatic and aromatic amino acids.

TEST CONDITIONS (MERCK METHOD)

5.0 ml Hemoglobin acc. to Anson (20 mg/ml dissolved in HCl 0.06 mol/l pH 1.6
1.0 ml Pepsin (Cat. No. 7185: 0.66 mg/ml; Cat. No. 7192: 0.05 mg/ml), dissolved in HCl 0.06 mol/l pH 1.6.
Incubate exactly for 10 minutes at 25° C., then add 10.0 ml 4% Trichloroacetic acid, dissolved in redistilled water.
After filtration mix
3.0 ml Filtrate
20.0 ml Redistilled water
1.0 ml NaOH 3.85 mol/l
1.0 ml Folin reagent After an incubation of cca 15 min. measurement of A at 546 nm against blank. Calibration with tyrosine solutions.

1 FIP - unit is defined as the quantity of enzyme which under test conditions liberates 1 $\mu$mole of Folin-positive amino acids per minute (calculated as tyrosine).

The product obtained from pepsin is an acid active enzyme. Therefore this procedure of preparation of an enzymatic product from the byproducts of a food pharmaceutical grade of pepsin has application in the leather industry as an acid bating product.

The hydrolyzed protein components in the by-products assure a better stabilization of the pepsin activity and do not require the addition of other agents. NaCl is used as preserving agent and the high content of lipids in the enzymatic product eliminates the dusting formation during the drying process.

In accordance with the present invention, the proteolytical enzyme with an optimum activity under acid conditions has the ability to break the peptide chains of the hide structure at a pH of around 2.0 to 2.4 even if the hides were already chrome tanned.

The enzyme has an effect of peptization of the dermal fiber structure without any danger of loosening the grain, because of separation of the papillar layer from the reticular layer.

This pepsin enzyme prepared in accordance with the present invention works more gently than the alkaline proteolytic enzyme and can be used at lower temperatures such 20-25° C. Furthermore running time is not critical compared to alkaline bating where the enzyme activity is sensitive to both temperature and running time.

According to the present invention:

a: The acid enzyme treatment can be done after pickling,—in the pickle bath—as described below in Example 1. Replacing the present classical alkaline bating process will result in additional softness of the leather, without the danger of looseness which is characteristic of the bating under alkaline conditions.

b: The acid enzyme treatment can be done on the wet blue chrome tanned stock after the shaving operation. In this case in addition to softer leather, an increase of surface yield of 3-5% is obtained and also better color uniformity of the leather is observed.

After shaving, the hides are thinner, therefore the diffusion, and penetration of the pepsin enzyme through the inner layer is much faster and more effective than during the alkaline bating when the hides are thicker.

This acid enzyme product, according to the present invention works more efficiently at pH 2±0.2. The wet blue stock has generally a pH 3.2 to 4.2 according to the tannery procedure. Therefore prior to the acid enzymatic treatment, the shaved wet blue stock has to be washed twice to eliminate the chrome salt which is not fixed to the hide and may inhibit the enzyme activity.

The procedure is better described in Example 3. After washing, the wet blue hides are acidified to pH 2±0.2 preferably with HCl or formic acid, phosphoric acid but not with sulfuric acid or oxalic acid which can strip the chrome.

At this stage, the acid bating enzyme of the present invention is added and the drum is run for 2 hours or overnight and in this case at lower temperature of 20° to 25° C., as discovered in the examples below.

After the acid enzymatic treatment the float is drained and the hides are washed for 10 minutes with water at 35° C. and then the tannery processes of neutralizing, coloring, retaining and fat liquoring are continued.

EXAMPLE 1

Five limed hides- that means after soaking and dehairing—were sided left and right, marked each one separately for identification then weighed. The left sides were the controls of our processes according to the tannery procedure.

The five right sides were processed in a wood drum as follows:
1. Wash 100% float 90° F. for 15 min. Drain.
2. 100% float 90° F., add 2.5% ammonium sulfate and the drum was rotated for 30 minutes. Then 0.5% formic acid is added; continue rotating the drum for another 30 minutes. The pH was checked to read a pH around 8 and the section was completely colorless to phenolphthaelin.
3. The sides were then washed twice with 100% float 90° F., running each time for 10 minutes and drained.
4. The drum was filled with 30% float at 80° F. and 6% salt by hide weight. After 10 min. of rotating the drum, the salimeter was 28°, if less, additional salt should be added.
5. At this time, 0.75 formic acid (1:10) was added and the drum was rotated for 30 minutes, then 1.75% sulfuric acid 66% diluted 1:10 water was added in two feeds every 15 min., then the drum was run for another 2 hours until pH 2±0.2 was achieved. If necessary additional sulfuric acid should be added until pH 2±0.2 is achieved. Instead of sulphuric acid hydrochloric acid can also be used.
6. Acid bating: at this stage 2% of acid enzyme with activity of 0.2–0.6 FIP units/mg, according to the present invention is added in the drum and continue rotating for 2 hours.
7. Then 0.75% sodium formate was added and the drum was rotated for 15 mins, pH was 2.7–2.8, then continue with the tannery process of chrome tanning.

The wet blue sides were then wrung, mixed with the left sides control, inspected, then split, shaved as per tannery requirements and continue with the regular tanning procedure.

By visual inspection of the sides in crust condition, tighter and more uniform color of the right treated sides were observed.

EXAMPLE 2

Ten pigskins in lime condition were delimed as described in Example No. 1, paragraphs 1 and 2, then:
3. The pigskins were washed twice with 100% float at 70° F. for 15 min and for the second washing were added 1% surfacctant to remove the excess grease and run for another 15 min. The float was drained and in a new float continue with the pickle process.
4. The drum was filled with 150% float at 80° F. and 8% salt on limed weight was added to achieve minimum 28° salimeter, if less, additional salt should be added.
5. At this time 0.75% formic acid, diluted 1:10 was added and the drum was rotated for 30 mins. Then 1% HCl 36%, diluted 1:10 was added in the two feeds, 15 mins. apart and the drum was run for 4 hours. The pH of 2.2±0.2 was achieved, if necessary, additional HCl should be added.
6. Acid bating: at this stage 2% pepsin enzyme product, with activity 0.2 to 0.6 FIP units/mg, according to the present invention was added to the drum and continue rotating for 4 hours or overnight.
7. 0.75% sodium formate was added and the drum was rotated for 15 mins.; the pH of 2.7–2.9, was achieved. Then continue the process of chrome tanning and all other steps according to the process flow to the crust condition.

Beside more uniform color on the entire surface of the pigskins, a softer leather was obtained.

EXAMPLE NO. 3

Five wet blue hides were marked each one for identification from 1 to 5 on both sides left and right, then sided, split and the surface area measured. Then the sides were shaved according to the tannery equipment 1.2 to 1.4 mm and weighed, while keeping separate the left sides as controls, and the right sides for test were processed in a wood drum, according to the present invention as follows:
1. Washed with 100% float at 35° C. for 10 min. Then drained.
2. Repeat the washing for the second time with 100% float at 35° C. for another 10 min. and drain completely.
3. In a new float 100%, at 35° C., 1% HCl 36%, diluted 1:10 with water, was added slowly during 15 min periods and the drum was rotated for 30 min. until a pH of 2.0±0.2 was achieved.

If necessary additional HCl 36% is added and continue to run the drum for another 15 min to achieve the pH of 2±0.2.
4. Acid enzymatic treatment: 2% of acid pepsin enzyme product was added and the drum was rotated for 2 hours.
5. The float was drained and the sides were washed with 100% float at 35° C. for 10 min.
6. In a new float of 100%, 35° C., 0.75% sodium formate was added and the drum was run for 15 mins., the pH was 3.4–3.6. The test sides were mixed with the control sides and the regular tanning process of neutralizing, coloring, retanning and fatliquoring was completed.

The sides were dried through the pasting dryer, then the left control sides were sorted from the test right sides. Each side was measured and a surface yield increase of 3.5% was observed.

The sides were then evaluated with results as follows:
The higher yield increase of the test leather versus control, a pronounced softness and temper uniformity; also, tighter leather on the entire surface and more uniform color. All physical-chemical characteristics were comparable.

| | | (fig. no. 3) | | | |
|---|---|---|---|---|---|
| | | Wet-blue sides | | Finished leather | % area increase | Area/lb |
| | | lbs. | sq. ft. | sq. ft. | | |
| 1. | Left-Control | 13.50 | 24.1 | 25.0 | 3.73 | 1.86 |
| | Right-Test | 13.00 | 22.3 | 24.2 | 8.50 | 1.86 |
| 2. | Left-Control | 14.00 | 25.0 | 27.1 | 8.00 | 1.93 |
| | Right-Test | 13.75 | 24.0 | 27.0 | 12.50 | 1.96 |
| 3. | Left-Control | 11.00 | 19.2 | 19.3 | 0.50 | 1.75 |
| | Right-Test | 11.00 | 19.2 | 21.2 | 10.40 | 1.93 |
| 4. | Left-Control | 12.00 | 22.1 | 23.2 | 5.00 | 1.93 |
| | Right-Test | 12.50 | 23.0 | 25.2 | 9.50 | 2.02 |
| 5. | Left-Control | 12.00 | 21.1 | 22.2 | 5.20 | 1.86 |

-continued

| | Right-Test | 12.50 | 23.0 | 25.1 | 9.10 | 2.00 |
|---|---|---|---|---|---|---|

1) Total increase in area:
(sq. ft of finished leather/sq. ft. of wet-blue)

CONTROL
- area in wet-blue = 111.5 sq. ft.
- area in finished leather = 116.8 sq. ft.
- Yield area increase = 4.75%

TEST
- area in wet-blue = 111.5 sq. ft.
- area in finished leather = 122.7 sq. ft.
- Yield area increase = 10.04%

Total area yield test versus control on finished leather:
10.04% − 4.75% = 5.29%

2) Total yield increase area versus weight:
(sq. ft. of finished leather/lb)

Wet-blue surface
- C = 111.5 sq. ft.
- T = 111.5 sq. ft.

Wet-blue weight
- C = 62.5 lb.
- T = 62.7 lb.

$S_{Wb}/W_{Wb}$
- C = 1.78
- T = 1.77

Finished Surface
- C = 116.8 sq. ft.
- T = 122.7 sq. ft.

Wet-blue weight
- C = 62.5 lb.
- T = 62.7 lb.

$S_F/W_{Wb}$
- C = 1.86
- T = 1.95

Increase of area versus weight:
$C_F/C_{Wb}$ = 1.86/1.78 = 4.49%
$T_F/C_{Wb}$ = 1.95/1.77 = 10.16%
Total increase = 10.16 − 4.49 = 5.67%

| | Control | Test | Yield increase test/control |
|---|---|---|---|
| Total area increase % | 4.75 | 10.04 | 5.29 |
| Total area increase versus weight of wet-blue % | 4.49 | 10.16 | 5.67 |

$S_{Wb}$ = Surface wet blue
$S_F$ = Surface finished
$W_{Wb}$ = Weight wet blue
$C_F$ = Control finished
$T_F$ = Test finished In one of the largest tanneries the test were conducted match sides on twelve wet blue hides 1.6 to 1.8 mm, left and right, that means control versus test. The results obtained in this tannery were:

1) % yield increase: sq. ft. of finished leather/sq. ft of wet-blue

| | Total lbs wet-blue | Total sq. ft. wet-blue | Total sq. ft.- finished leather | % yield increase finished/wet-blue | Total yield increase % |
|---|---|---|---|---|---|
| CONTROL | 149.7 | 263.0 | 279.6 | 6.3 | |
| TEST | 147.7 | 257.8 | 284.1 | 10.2 | 3.9 |

2) % yield increase: sq. ft. of finished leather/lbs.

| | Wet-blue surface | Wet-blue lbs | Total sq. ft/lb w-b/w-b | Finished surface | Total sq. ft/lb. fin/w-b | 5/3 | Total field increase, % |
|---|---|---|---|---|---|---|---|
| | 0 | 1 | 2 | 3 | 4 | 5 | 6 | 7 |
| CONTROL | 263.0 | 149.7 | 1.766 | 279.6 | 1.87 | 6.25% | — |
| TEST | 257.8 | 147.7 | 1.751 | 284.1 | 1.92 | 9.7% | 3.5% |

For a tannery which processes one thousand hides/day (or 2000 sides/day), an average of 3.5% yield increase will result in an additional 3 million sq. feet a year.

Chemical analysis of the sides of hides processed according to the invention shows that the enzymatic treatment under acid conditions has no negative influence concerning the chromium content, and a decrease in grease after this treatment was observed for the hides, particularly sheepskin or pigskins.

| | WET BLUE HIDES | CRUST LEATHER | CONTROL TEST |
|---|---|---|---|
| $Cr_2O_3$ | 3.82% | 3.80% | 3.72% |

The physical tests of crust leather are comparable (tensile strength, tear strength have normal value and the percentage of elongation due to determinated load and elongation to rupture or break was higher by about 5–10%).

The higher yield increase of the test leather versus control, a pronounced softness and temper uniformity; also, tighter leather on the entire surface and more uniform color are advantageous. All physical-chemical characteristics were comparable.

EXAMPLE 4

Hides tanned in accordance with Example 3 (until step 4), processed with 2% pepsin enzyme product and after the drum was rotated for 15 min. and were kept overnight with 5 minute agitation every 2 hours. In this case the float temperature was 22° to 25° C.

Under such conditions, where the treatment with acid pepsin enzyme was done overnight at lower temperature, the leather in crust condition was much softer and higher surface yield was obtained. Also, the elongation test showed a 10% increase over the hides which were processed according to Example No. 3 where the hides were kept only 2 hours in enzymatic treatment. Also, by visual inspection the grain was smoother, especially the neck was more relaxed, and there was a more uniform temper and better color uniformity.

EXAMPLE 5

Hides tanned in accordance with Example 1 (which were not bated in alkaline condition, but in the pickle condition) were processed after shaving in accordance with Example 3 with the purpose to compare the hides which were bated in the pickle condition to those treated with the acid enzyme after chrome tanning when hides were already shaved.

This acid bating procedure has the advantages that the grain is tighter, with better temper and color uniformity and a greater increase in surface yield is obtained.

EXAMPLE 6

The chrome tanned splits after shaving were processed in accordance with Example 4.

The splits after drying to the crust condition were much softer, with uniform temper and color over the entire surface. Another advantage of the splits treated with acid pepsin enzyme was that a higher surface yield was also observed.

EXAMPLE 7

The pigskins which were processed according to the tannery procedure, bated in alkaline condition or in accordance with Example 2 were charged to the retanning, coloring drums for an acid enzymatic treatment of chrome tanned (wet-blue) stock.

The procedure was in accordance with Example No. 3. For nappa, garment, or upholstery pigskins, the rotating time during the acid enzymatic treatment can be extended to 4 hours or overnight.

Because of better degreasing the color was more uniform over the entire surface and the skins were softer with a clearer grain surface.

EXAMPLE 8

For furskins, after the main soaking, in a paddle where the float was 600%, temperature 25° C., 15–20 g/l salt and 1.5 to 2.0 g/l acetic acid until a pH of about 3 is achieved. The skins are agitated for 4 hours. At this stage 1–1.5 g/l acid enzyme in accordance with the present invention was added, and the skins were agitated in the paddle for another 6–8 hours. In the same float was added 1.5 to 2 g/l formic acid, and after an agitation of 30 minutes of the furskins, 0.6 to 0.8 g/l $H_2SO_4$ (diluted 1:10) were added and the agitation was continued for another 8 to 10 hours.

Instead of acetic acid other organic acids can be used, and instead of sulfuric acid, hydrochloric acid can be used.

One of the biggest observed advantages of this treatment was a lighter weight of the fur, caused by removal of natural fat and a significant improvement in softness.

EXAMPLE 9

For the furskins already chrome tanned, the enzyme in accordance with the present invention, can be used before the coloring and fatliquoring process as follows: the chrome tanned furskins were introduced in a paddle with a float of 400 to 600%, temperature 20°–25° C. and 1 to 1.2 g/l HCl 1 was added until a pH of 2.4–2.6 was reached. After an agitation of 30 minutes, 1.5 to 2 g/l acid enzyme product in accordance with the present invention was added and the skins were agitated for 4–6 hours, then continue with the coloring and fatliquoring processes.

By this treatment much softer furskins were obtained.

What is claimed is:

1. A process for preparing a dry enzymatic product with a proteolytic activity of 0.2 to 0.6 units FIP/mg of pepsin extract, suitable for acid bating of a hide, which comprises the steps of:
   (a) macerating bovine, ovine or porcine red stomach mucous in an acid to obtain a liquid enzymatic extract containing 16 to 18% dry matter;
   (b) sedimenting the liquid enzymatic extract prepared in step (a) to form three distinct phases, each having a different density, the middle phase of which is clear and suitable to produce a pharmaceutical containing pepsin, while the other two phases are by-products also containing pepsin;
   (c) separating the clear middle phase containing the pepsin and having a proteolytic activity of 0.15 to 0.2 units FIP/ml from the other two phases;
   (d) combining the two by-product phases formed during step (b) to obtain a liquid pepsin-containing product having a proteolytic activity of 0.10 to 0.15 units FIP/ml and 15 to 18% dry matter; and
   (e) drying the liquid pepsin-containing product obtained in step (d) to yield the dry enzymatic product suitable for bating a hide.

2. The process for preparing the dried enzymatic product defined in claim 1 wherein according to step (a) the acid employed is 37% HCl and wherein during the macerating process the liquid enzymatic extract is continuously agitated until a pH of 2 to 2.5 is obtained.

3. The process for preparing the dried enzymatic product defined in claim 1 wherein according to step (e) the liquid pepsin-containing product is dried by an atomizer or by blowing air.

4. The process for preparing the dried enzymatic product defined in claim 1 wherein following step (e) the dried enzymatic product is dry mixed with 10 to 20% NaCl for preservation, then ground, weighed and packed.

* * * * *